US 9,993,316 B2

(12) United States Patent
Owen

(10) Patent No.: US 9,993,316 B2
(45) Date of Patent: *Jun. 12, 2018

(54) BRACKET SYSTEM

(71) Applicant: Brandon Owen, Fort Collins, CO (US)

(72) Inventor: Brandon Owen, Fort Collins, CO (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/648,305

(22) Filed: Jul. 12, 2017

(65) Prior Publication Data
US 2017/0304026 A1   Oct. 26, 2017

Related U.S. Application Data

(63) Continuation of application No. 15/345,368, filed on Nov. 7, 2016, now Pat. No. 9,707,057, which is a continuation of application No. 14/491,875, filed on Sep. 19, 2014, now Pat. No. 9,486,299.

(60) Provisional application No. 61/880,322, filed on Sep. 20, 2013.

(51) Int. Cl.
| | |
|---|---|
| *A61C 7/28* | (2006.01) |
| *A61C 7/14* | (2006.01) |
| *A61C 7/20* | (2006.01) |
| *A61C 7/00* | (2006.01) |
| *A61C 7/30* | (2006.01) |

(52) U.S. Cl.
CPC ................ *A61C 7/146* (2013.01); *A61C 7/00* (2013.01); *A61C 7/002* (2013.01); *A61C 7/14* (2013.01); *A61C 7/145* (2013.01); *A61C 7/20* (2013.01); *A61C 7/287* (2013.01); *A61C 7/28* (2013.01); *A61C 7/303* (2013.01)

(58) Field of Classification Search
CPC ........... A61C 7/14; A61C 7/143; A61C 7/148; A61C 7/28; A61C 7/287; A61C 7/12; A61C 7/303
See application file for complete search history.

(56) References Cited

U.S. PATENT DOCUMENTS

| | | |
|---|---|---|
| 2,716,283 A | 8/1955 | Atkinson |
| 4,494,931 A | 1/1985 | Wildman |
| 4,948,366 A | 8/1990 | Horn et al. |
| 5,098,288 A | 3/1992 | Kesling |

(Continued)

FOREIGN PATENT DOCUMENTS

| | | |
|---|---|---|
| EP | 1 830 735 | 9/2007 |
| WO | WO 2007/087697 | 8/2007 |

OTHER PUBLICATIONS

U.S. Appl. No. 61/880,322, filed Sep. 20, 2013.
(Continued)

*Primary Examiner* — Julianna N Harvey
(74) *Attorney, Agent, or Firm* — Craig R. Miles; CR Miles P.C.

(57) ABSTRACT

A bracket system for orthodontic appliances including a bracket combinatorial library having a plurality of brackets each interchangeably fixedly mountable to each of a plurality of teeth within a dentition group in a dental arch, whereby the plurality of brackets can be configured to provide incremental variation in tipping force moments, in-out force moments, and torqueing force moments over the entire useful range of orthodontic mechanics, allowing an orthodontic practitioner to prescribe a combination of tipping force moments, in-out force moments, and torqueing force moments unique for each tooth in relation to the plurality of teeth of a patient.

20 Claims, 9 Drawing Sheets

(56) References Cited

U.S. PATENT DOCUMENTS

| | | |
|---|---|---|
| 5,248,257 A | 9/1993 | Cannon |
| 5,447,432 A | 9/1995 | Andreiko et al. |
| 5,464,347 A | 11/1995 | Allesee |
| 5,464,349 A | 11/1995 | Andreiko et al. |
| 5,542,842 A | 8/1996 | Andreiko et al. |
| 5,683,243 A | 11/1997 | Andreiko et al. |
| 6,015,289 A | 1/2000 | Andreiko et al. |
| 6,206,690 B1 | 3/2001 | Vargas |
| 6,244,861 B1 | 6/2001 | Andreiko et al. |
| 6,247,923 B1 | 6/2001 | Vashi |
| 6,347,939 B2 | 2/2002 | Abels |
| 6,394,798 B1 | 5/2002 | Huff et al. |
| 6,592,367 B2 | 7/2003 | Kyritsis |
| 6,616,444 B2 | 9/2003 | Andreiko et al. |
| 6,632,089 B2 | 10/2003 | Rubbert et al. |
| 6,776,614 B2 | 8/2004 | Wiechmann et al. |
| 7,155,373 B2 | 12/2006 | Jordan et al. |
| 7,160,107 B2 | 1/2007 | Kopelman et al. |
| 7,223,099 B2 | 5/2007 | Niederwanger et al. |
| 7,229,282 B2 | 6/2007 | Andreiko et al. |
| 7,326,051 B2 | 2/2008 | Miller |
| 7,766,653 B2 | 8/2010 | Manemann et al. |
| 7,850,451 B2 | 12/2010 | Wiechmann et al. |
| 8,113,828 B1 | 2/2012 | Greenfield |
| 8,353,699 B2 | 1/2013 | Johnston |
| 9,486,299 B2 | 11/2016 | Owen |
| 9,707,057 B2 | 7/2017 | Owen |
| 2002/0010568 A1 | 1/2002 | Rubbert et al. |
| 2004/0115586 A1 | 6/2004 | Andreiko et al. |
| 2005/0186525 A1 | 8/2005 | Abels et al. |
| 2005/0244774 A1 | 11/2005 | Abels et al. |
| 2007/0128571 A1 | 6/2007 | Kimura |
| 2007/0259300 A1 | 11/2007 | McLaghlin et al. |
| 2007/0259302 A1 | 11/2007 | Jayawardena |
| 2008/0057459 A1 | 3/2008 | Abels et al. |
| 2008/0070184 A1 | 3/2008 | Farzin-Nia et al. |
| 2008/0311534 A1 | 12/2008 | Farzin-Nia et al. |
| 2009/0004617 A1 | 1/2009 | Oda et al. |
| 2009/0004619 A1 | 1/2009 | Oda et al. |
| 2009/0117511 A1 | 5/2009 | Minium |
| 2009/0155734 A1 | 6/2009 | Damon |
| 2009/0162807 A1 | 6/2009 | Hagenganz et al. |
| 2010/0173256 A1 | 7/2010 | Rodriguez et al. |
| 2010/0196839 A1 | 8/2010 | Stevens |
| 2010/0297569 A1 | 11/2010 | Huang et al. |
| 2011/0014583 A1 | 1/2011 | Romano et al. |
| 2011/0020762 A1 | 1/2011 | Kanomi et al. |
| 2011/0033811 A1 | 2/2011 | Swain |
| 2011/0097682 A1 | 4/2011 | Curiel et al. |
| 2011/0151391 A1 | 6/2011 | Shih et al. |
| 2012/0015315 A1 | 1/2012 | Wiechmann et al. |
| 2012/0225398 A1 | 9/2012 | Fallah |
| 2012/0308952 A1 | 12/2012 | Cosse |
| 2012/0322019 A1 | 12/2012 | Lewis |
| 2013/0040260 A1 | 2/2013 | Bukhary |

OTHER PUBLICATIONS

PCT International Patent Application No. PCT/US2014/056679; International Search Report dated Jan. 2, 2015, 15 total pages.

PCT International Patent Application No. PCT/US14/58982, filed Oct. 3, 2014.

PCT International Patent Application No. PCT/US14/58982; International Search Report dated Jan. 14, 2015, 10 total pages.

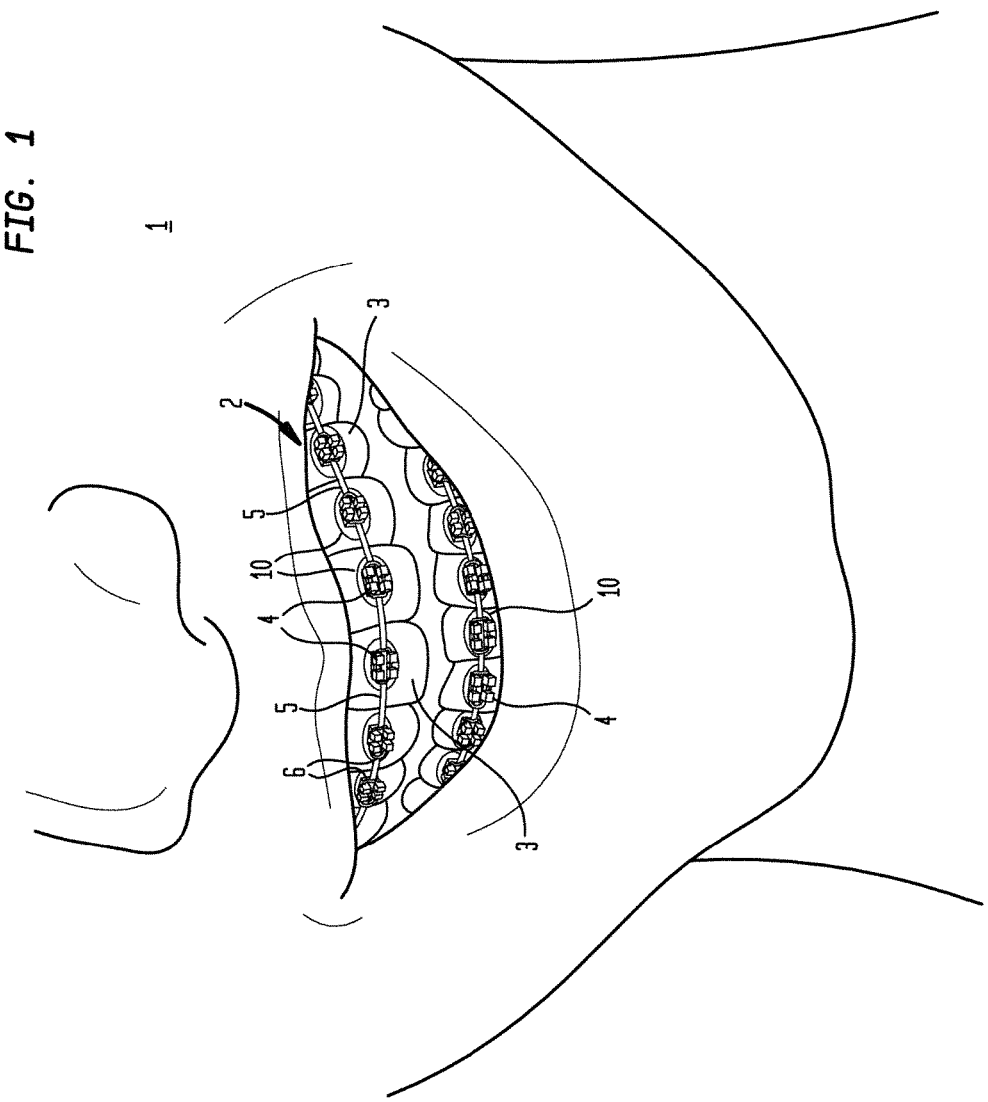

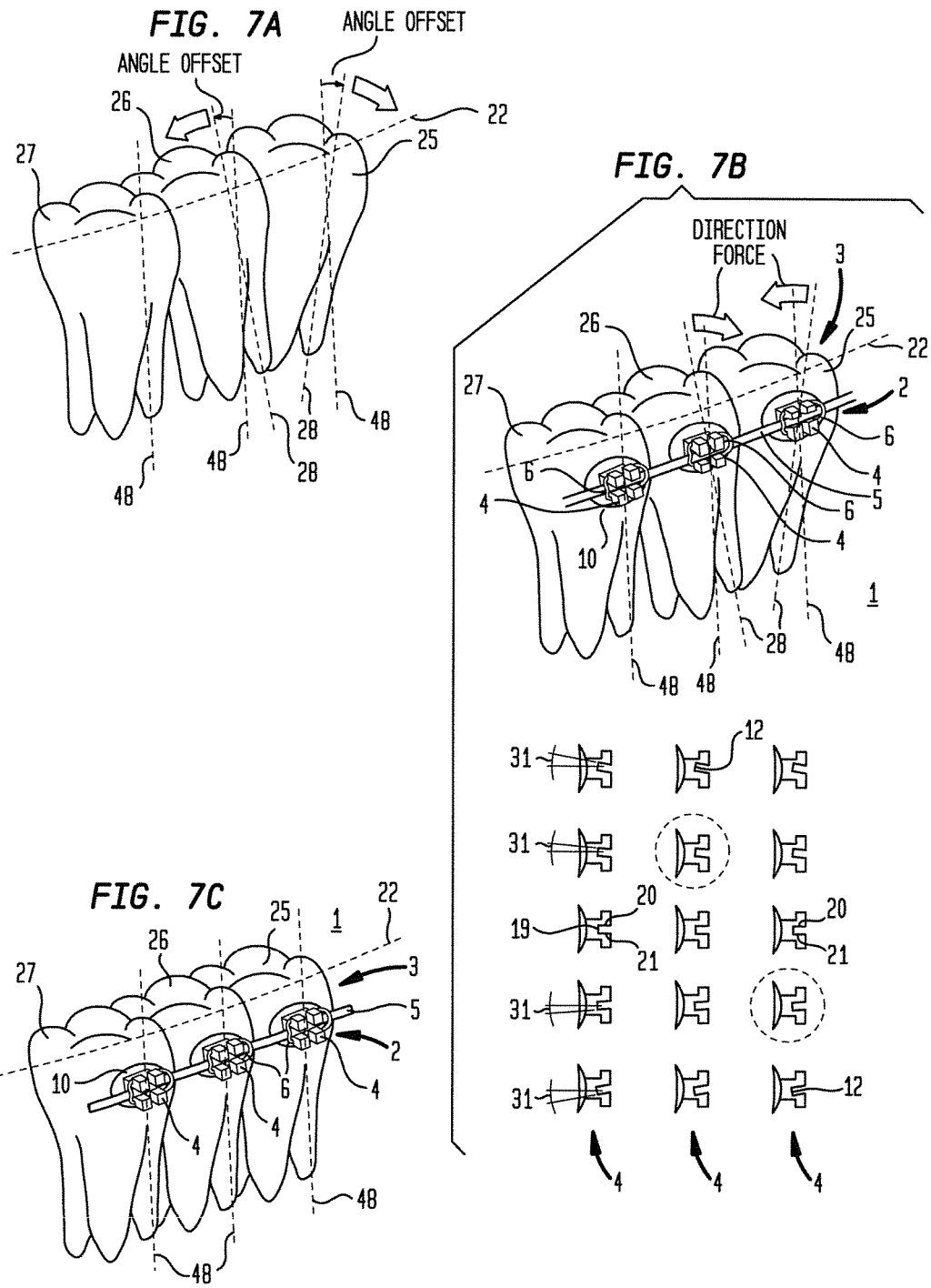

BRACKET SYSTEM

This United States Patent Application is a continuation of U.S. patent application Ser. No. 15/345,368, filed Nov. 7, 2016, now U.S. Pat. No. 9,707,057, issued Jul. 18, 2017, which is a continuation of U.S. patent application Ser. No. U.S. patent application Ser. No. 14/491,875, filed Sep. 19, 2014, now U.S. Pat. No. 9,486,299, issued Nov. 8, 2016, which claims the benefit of U.S. Provisional Patent Application No. 61/880,322, filed Sep. 20, 2013, each hereby incorporated by reference herein.

I. FIELD OF THE INVENTION

A bracket system for orthodontic appliances including a bracket combinatorial library having a plurality of brackets each interchangeably fixedly mountable to each of a plurality of teeth within a dentition group in a dental arch, whereby the plurality of brackets can be configured to provide incremental variation in tipping force moments, in-out force moments, and torqueing force moments over the entire useful range of orthodontic mechanics, allowing an orthodontic practitioner to prescribe a combination of tipping force moments, in-out force moments, and torqueing force moments unique for each tooth in relation to the plurality of teeth of a patient.

II. BACKGROUND OF THE INVENTION

Orthodontic treatment applied to straighten or align teeth of a patient dates back hundreds of years. Generally, orthodontic treatment includes the use of wires wrapped around the teeth of a patient. Around the mid-1970s, chiefly due to improvements in adhesive technology, the preferred method shifted to bonding brackets directly onto the teeth of the patient and running elastic archwires of rectangular cross-sectional shape through archwire slots disposed within the brackets.

Typically, manual selection of orthodontic appliance components may be made by an orthodontic practitioner from available inventories of standard or otherwise pre-manufactured components, which the orthodontic practitioner assembles to form the orthodontic appliance to treat the patient. In most cases, the appliance components, such as the brackets, may be adapted to a certain tooth, for instance an upper canine, but not to the individual tooth of the specific patient. Adaptation of the bracket to the individual tooth of the specific patient may commonly be performed by filling the gap between the individual tooth surface and the bracket surface with adhesive to thereby bond the bracket to the individual tooth such that the archwire slot orients in a horizontal plane when the teeth move to a targeted position, whereby the driving force for moving the teeth to the targeted position is provided by the archwire disposed within the archwire slots.

As stated above, conventional brackets may typically be designed and manufactured based upon average anatomy. Consequently, orthodontic practitioners select what they perceive to be the brackets and archwires having a relatively similar design to that required to treat a particular patient, then modify the design to treat the particular patient. Some modifications may be performed when the orthodontic appliance is initially installed, but almost inevitably, modification is required during the course of treatment of the patient. These subsequent modifications may take the form of replacement of brackets, but most commonly take the form of periodic bending and reshaping of the archwire as the treatment progresses. Thus, the treatment of the patient has become a manual feedback system in which the orthodontic practitioners monitors the progress of the treatment and then readjusts the orthodontic appliance to correct the forces being applied to the teeth to bring the teeth to targeted positions. As a result, the patient may be subjected to treatment over a period of time which may be greater than would be necessary if the orthodontic appliance were initially optimally designed. In addition, the time required of the orthodontic practitioner for implementation of the treatment may be several times greater than if modification of the orthodontic appliance was not needed. Hence, the orthodontic practitioner may be restricted to treating fewer patients and the cost of the treatment to the patient and/or to the orthodontist may be increased.

Systems and methods for providing custom orthodontic appliances are gaining acceptance. Typically, these systems and methods take into account individual patient anatomy and design and manufacture custom appliances on a case-by-case basis. Often, custom appliance designs are based on calculated ideal occlusions or treatment plans by or with the aid of computers or computer programs, whereby tooth setups or post-treatment tooth positions may be determined based on digital data of the tooth shapes and other dental anatomy of the individual patient. The resulting custom appliances, when properly designed and manufactured, can be fitted to the teeth of a patient by an orthodontic practitioner, usually using custom jigs or other positioning devices or techniques that may be provided with the custom appliances to insure placement at predetermined positions on the teeth so that the orthodontic appliance functions as it was designed to. Properly installed, such a custom appliances can move the teeth of a patient in less time and with a minimum of post-installation manipulation by the orthodontic practitioner.

However, custom orthodontic appliances may not always be available or may not always be desired, for example because the design and manufacturing can be relatively expensive and time-consuming.

Accordingly, a need exists for a system and method which can improve the selection and customization of standard or otherwise pre-manufactured orthodontic appliance components to achieve the entire useful range of orthodontic mechanics in a cost-effective and timely fashion.

III. SUMMARY OF THE INVENTION

A broad object of a particular embodiment of the invention can be to provide a bracket system for orthodontic appliances including a bracket combinatorial library having a plurality of brackets each interchangeably fixedly mountable to each of a plurality of teeth within a dentition group in a dental arch, whereby the plurality of brackets can be configured to provide incremental variation in tipping force moments, in-out force moments, and torqueing force moments over the entire useful range of orthodontic mechanics.

Another broad object of a particular embodiment of the invention can be to provide a method of producing a bracket system by providing a bracket combinatorial library having a plurality of brackets each interchangeably fixedly mountable to each of a plurality of teeth within a dentition group in a dental arch, whereby the plurality of brackets can be configured to provide incremental variation in tipping force moments, in-out force moments, and torqueing force moments over the entire useful range of orthodontic mechanics.

Another broad object of a particular embodiment of the invention can be to provide a method of using a bracket system having a bracket combinatorial library by prescribing a unique combination of brackets from the bracket combinatorial library, each bracket within the bracket combinatorial library interchangeably fixedly mountable to each of a plurality of teeth within a dentition group in a dental arch; and fixedly mounting each bracket from the prescribed unique combination of brackets to each corresponding tooth of the plurality of teeth within the dentition group in the dental arch. The plurality of brackets can be configured to provide incremental variation in tipping force moments, in-out force moments, and torqueing force moments over the entire useful range of orthodontic mechanics.

Naturally, further objects of the invention are disclosed throughout other areas of the specification, drawings, and claims.

IV. BRIEF DESCRIPTION OF THE DRAWINGS

FIG. 1 is an illustration of an orthodontic appliance utilizing a particular embodiment of the inventive bracket system.

FIG. 7A is an illustration of torque misalignment of the teeth associated with facial-lingual inclination.

FIG. 7B is an illustration of the inventive bracket system fixed to respective surfaces of the teeth shown in FIG. 7A to correct torque misalignment of the teeth associated with facial-lingual inclination.

FIG. 7C is an illustration of the correction of torque misalignment of the teeth associated with facial-lingual inclination shown in FIG. 7B following treatment with the inventive bracket system.

V. DETAILED DESCRIPTION OF THE INVENTION

Figure 2A:
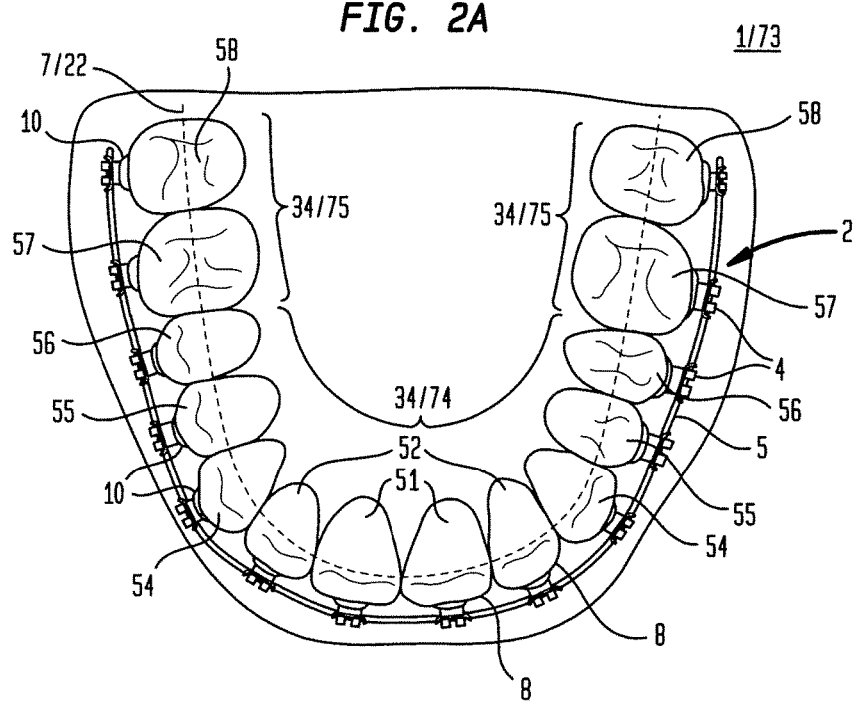
FIG. 2A is an illustration of a facial orthodontic appliance utilizing a particular embodiment of the inventive bracket system.
Figure 2B:
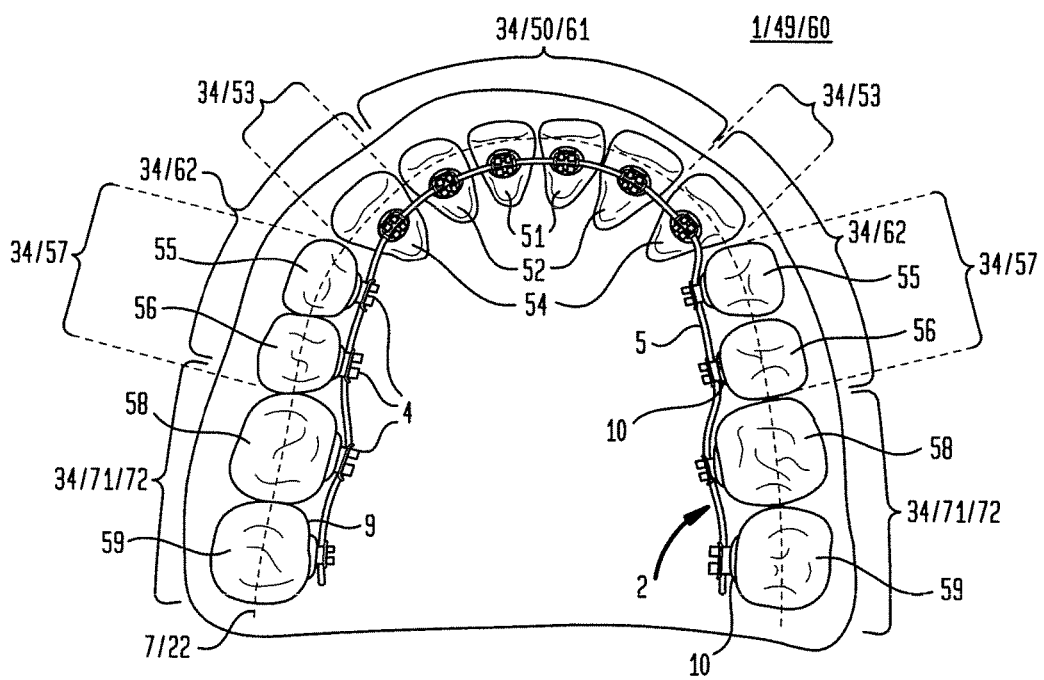
FIG. 2B is an illustration of a lingual orthodontic appliance utilizing a particular embodiment of the inventive bracket system.

Now referring primarily to FIG. 1, FIG. 2A, and FIG. 2B, embodiments of the inventive bracket system (1) can be utilized for orthodontic treatment performed by fixing an orthodontic appliance (2) to a plurality of teeth (3). Typically, an orthodontic appliance (2) includes three basic elements: a plurality of brackets (4), an archwire (5), and a ligature (6). Each of the plurality of brackets (4) can be adhered to a tooth surface (8)(9) and intercoupled by the archwire (5), whereby the the ligature (6) can be used to retain the archwire (5) in association with the plurality of brackets (4). The archwire (5) can generate external forces to urge the teeth (3) toward a targeted position or orientation over a period of time. Accordingly, the orthodontic appliance (2) can be utilized to correct malocclused teeth (3).

Now referring primarily to FIG. 2A, as to particular embodiments, the inventive bracket system (1) can include a plurality of brackets (4) which adhere to the facial surfaces (8) of respective teeth (3) around a dental arch (7), whereby the archwire (5) intercoupling the plurality of brackets (4) extends around the facial surfaces (9) of the teeth (3).

Now referring primarily to FIG. 2B, as to particular embodiments, the inventive bracket system (1) can include a plurality of brackets (4) which adhere to the lingual surfaces (9) of respective teeth (3) around the dental arch (7), whereby the archwire (5) intercoupling the plurality of brackets (4) extends around the lingual surfaces (9) of the teeth (3).

Figure 5A:
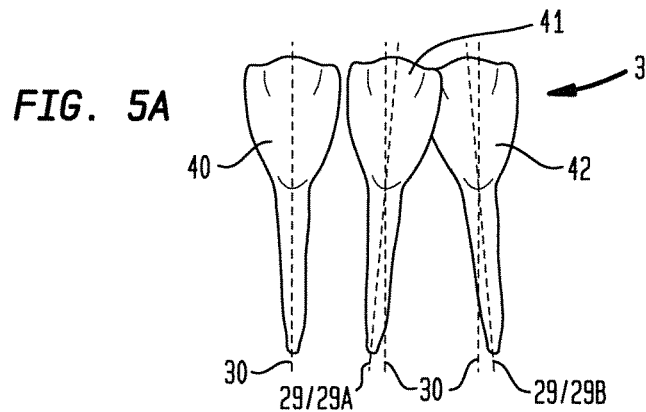
FIG. 5A is an illustration of tip misalignment of the teeth associated with mesial-distal inclination.
Figure 6A:
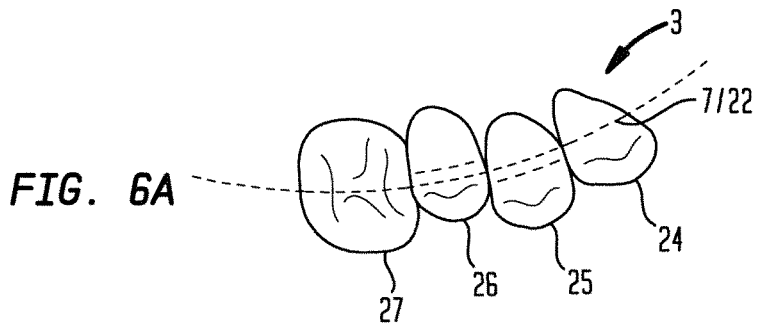
FIG. 6A is and illustration of in-out misalignment of the teeth in relation to the dental arch midline.

Now referring primarily to FIG. 5A, FIG. 6A, and FIG. 7A, embodiments of the inventive bracket system (1) can be utilized to correctly align a plurality of teeth (3), which can be malocclused or misaligned in relation to one or more of: mesial-distal inclination (29) (also referred to as "tip") (as shown in the example of FIG. 5A); a dental arch midline (22), whether facial or lingual misalignment (also referred to as "in-out") (as shown in the example of FIG. 6A), or facial-lingual root inclination (28) (also referred to as "torque") (as shown in the example of FIG. 7A).

Figure 3:
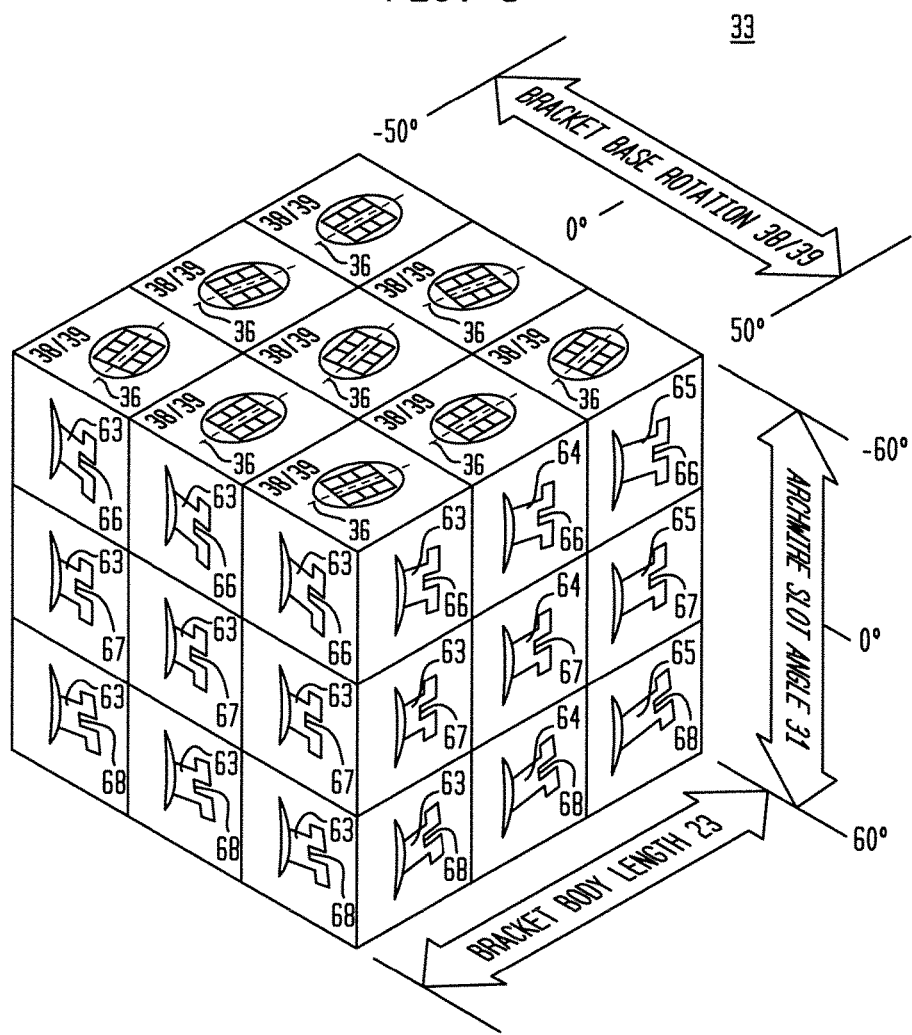
FIG. 3 is an illustration of a bracket combinatorial library having various combinations of bracket body lengths, archwire slot angles, and bracket base rotation configurations in a particular embodiment of the inventive bracket system.
Figure 4A:
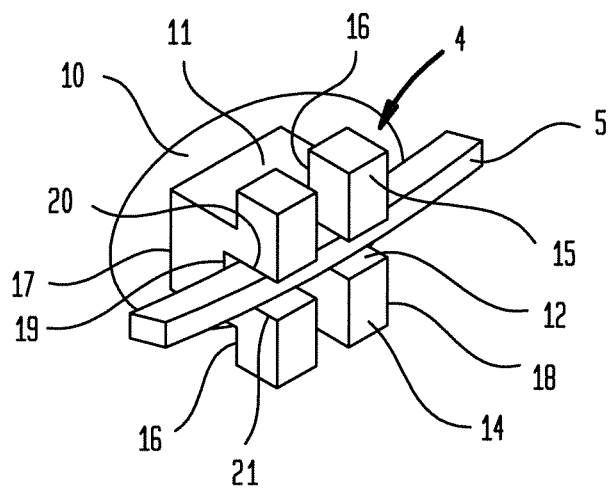
FIG. 4A is an illustration of a particular embodiment of a bracket of the inventive bracket system, whereby an archwire is disposed within an archwire slot of the bracket.
Figure 4B:
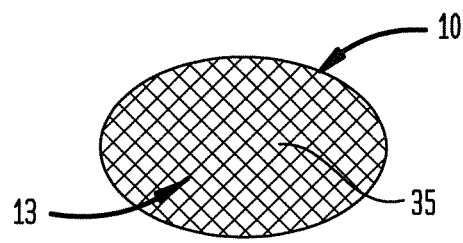
FIG. 4B is an illustration of a bracket base mounting surface having bond enhancement elements.

Now referring primarily to FIG. 3 through FIG. 4B, the inventive bracket system (1) can include a bracket combinatorial library (33) having a plurality of brackets (4) each interchangeably fixedly mountable to each of a plurality of teeth (3) within a dentition group (34) in a dental arch (7).

Each of the plurality of brackets (4) within the bracket combinatorial library (33) can include a bracket base (10), a bracket body (11), and an archwire slot (12).

The term "bracket combinatorial library" for the purposes of this invention means a plurality of brackets (4) having various combinations and permutations of bracket base rotation configurations (39), bracket body lengths (23), and archwire slot angles (31) over a maximum range of action for orthodontic mechanics to correspondingly provide a graded series of prescribable tipping force moments, in-out force moments, and torqueing force moments which can be customized for a respective tooth (3).

The bracket base (10) can have one configuration fixedly mountable to each one of the plurality of teeth (3) within the dentition group (34), whereby a bracket base mounting surface (35) can be adapted for directly bonding to the surfaces (8)(9) of respective teeth (3). As to particular embodiments, the bracket base mounting surface (35) can be configured to conform to a facial mountable tooth surface (8), a lingual mountable tooth surface (9), or both, of each one of the plurality of teeth (3) within the dentition group (34).

As to particular embodiments, the bracket base mounting surface (35) can be configured as a generally planar bracket base mounting surface (35). As to other particular embodiments, the bracket base mounting surface (35) can be configured as an arcuate bracket base mounting surface (35), which can have a concave or convex contour configured to conform to a corresponding convex or concave contour of a mountable tooth surface (8)(9) of each one of the plurality of teeth (3) within the dentition group (34).

Figure 5B:
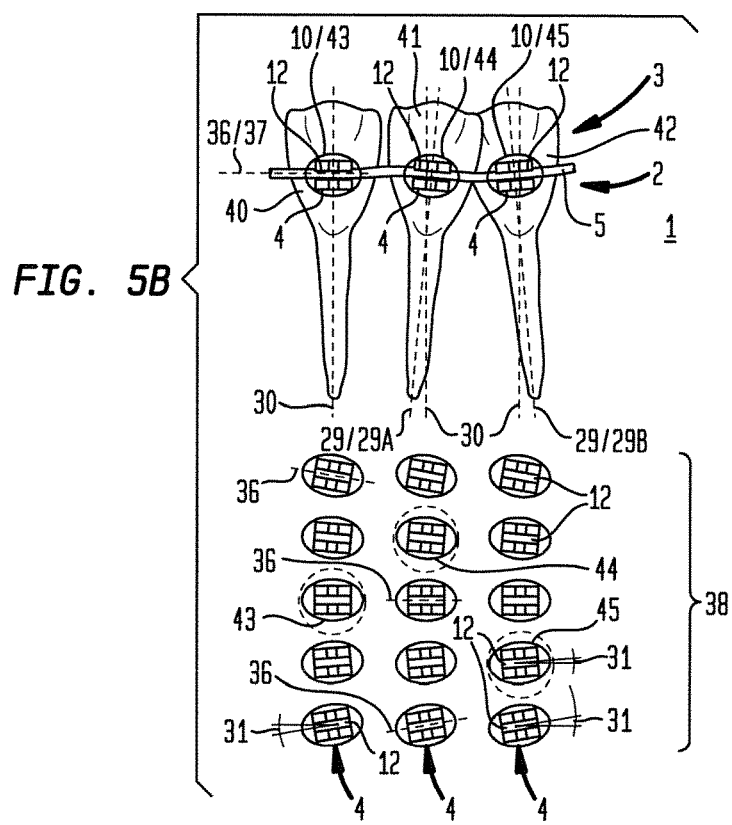
FIG. 5B is an illustration of the inventive bracket system fixed to respective surfaces of the teeth shown in FIG. 5A to correct tip misalignment of the teeth associated with mesial-distal inclination.
Figure 5C:
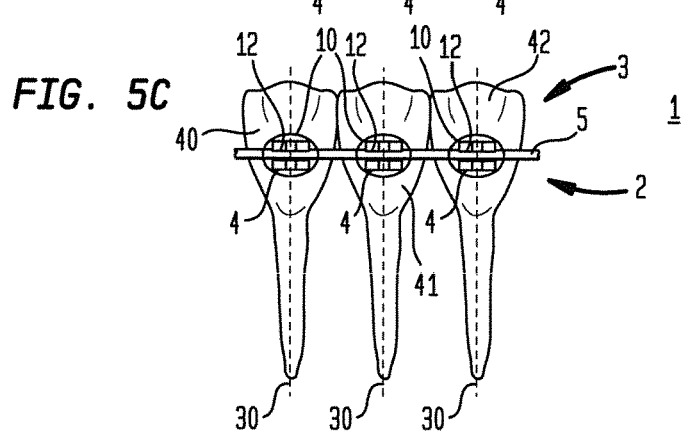
FIG. 5C is an illustration of the correction of tip misalignment of the teeth associated with mesial-distal inclination shown in FIG. 5B following treatment with the inventive bracket system.

Now referring primarily to FIG. 5A through FIG. 5C, the bracket base (10) can have a configuration rotatable in relation to a zero degree mesial-distal inclination axis (30) of a tooth (3) prior to being fixedly mounted to one of the plurality of teeth (3) within the dentition group (34). The bracket base (10) coupled to the bracket body (11) having an archwire slot (12) extending across a bracket body second end (18) can be rotated to dispose an archwire slot longitudinal axis (36) in a generally mesial-distal orientation, whereby the archwire slot (12) having the archwire slot longitudinal axis (36) in substantially perpendicular relation to the zero degree mesial-distal inclination axis (30) of the tooth (3) defines a zero degree archwire slot rotation axis (37). Tipping force moments can be generated by rotating the bracket base (10) and corresponding archwire slot (12) in either a clockwise or a counterclockwise direction from the zero degree archwire slot rotation axis (37) to provide a corrective archwire slot rotation configuration (38) (as shown in the example of FIG. 5B). The amount of rotation of the bracket base (10) and corresponding archwire slot (12) can be within the maximum range of action for orthodontic mechanics relating to correction of mesial-distal inclination (29) of one or more teeth (3). As an illustrative example, the bracket base (10) can have a configuration rotatable throughout a range of between about −50 degrees to about 50 degrees in relation to the zero degree archwire slot rotation axis (37), whereby an archwire slot rotation configuration (38) of −50 degrees, achieved by counterclockwise rotation from the zero degree archwire slot rotation axis (37), orients the corresponding archwire slot longitudinal axis (36) at about −50 degrees from the zero degree archwire slot rotation axis (37) and an archwire slot rotation configuration (38) of 50 degrees, achieved by clockwise rotation from the zero degree archwire slot rotation axis (37), orients the corresponding archwire slot longitudinal axis (36) at about 50 degrees from the zero degree archwire slot rotation axis (37). An archwire (5) can then be disposed within the archwire slot (12) to generate sufficient tipping force moments to correct mesial-distal inclination (29) of one or more teeth (3). The various bracket base rotation configurations (39) and corresponding archwire slot rotation configurations (38) can provide incrementally varying tipping force moments, whereby a greater a archwire slot rotation configuration (38) can generate greater tipping force moments in relation to a lesser archwire slot rotation configuration (38), which can generate lesser tipping force moments.

As shown in the illustrative example of FIG. 5A, a plurality of teeth (3) can be misaligned in relation to mesial-distal inclination (29), whereby a first tooth (40) can have substantially zero mesial-distal inclination (29), a second tooth (41) can have a distal-axial inclination (29A) of 5 degrees from the zero degree mesial-distal inclination axis (30), and a third tooth (42) can have a mesial-axial inclination (29B) of −5 degrees from the zero degree mesial-distal inclination axis (30). As shown in FIG. 5B, to correct this misalignment, bracket base rotation configurations (39) of the plurality of brackets (4) fixedly mounted to the corresponding plurality of teeth (3) can be prescribed (prescription shown in broken circle for each of the plurality of teeth (3)) such that sufficient tipping force moments can be generated by an archwire (5) disposed within the archwire slot (12) to move the plurality of teeth (3) toward the zero degree mesial-distal inclination axis (30).

As shown in FIG. 5B, to correct the mesial-distal inclination (29) of the second and third teeth (41)(42), a first bracket base (43) can be rotated and fixedly mounted to the first tooth (40) to orient the archwire slot longitudinal axis (36) of the corresponding archwire slot (12) in substantially parallel relation to the zero degree archwire slot rotation axis (37), which is in substantially perpendicular relation to the zero degree mesial-distal inclination axis (30) of the first tooth (40). A second bracket base (44), having a configuration which is similar to the first bracket base (43), can be rotated clockwise and fixedly mounted to the second tooth (41) to orient the archwire slot longitudinal axis (36) of the corresponding archwire slot (12) about 5 degrees from the zero degree archwire slot rotation axis (37). A third bracket base (45), having a configuration which is similar to the first and second bracket bases (43)(44), can be rotated counterclockwise and fixedly mounted to the third tooth (42) to orient the archwire slot longitudinal axis (36) of the corresponding archwire slot (12) about 5 degrees from the zero degree archwire slot rotation axis (37). An archwire (5) can then be disposed within each of the archwire slots (12) to generate sufficient tipping force moments to reduce the distal-axial inclination (29A) of the second tooth (41) and the mesial-axial inclination (29B) of the third tooth (42) toward zero degrees of mesial-distal inclination corresponding to the zero degree mesial-distal inclination axis (30) and provide a targeted alignment of the plurality of teeth (3) (as shown in the example of FIG. 5C). Accordingly, one rotatable bracket base configuration can be used to correct mesial-distal inclination (29) of a plurality of teeth (3) by rotating each bracket base (10) to achieve corresponding targeted archwire slot longitudinal axis (36) orientations configured to correct mesial-distal inclination of each tooth (3) within the plurality of teeth (3).

As to particular embodiments, the bracket base (10) can be provided with bond enhancement elements (13) to increase strength of the bond between the bracket base (10) and the respective tooth surfaces (8)(9). Bond enhancement elements (13) can include chemical bond enhancements, mechanical bond enhancements, or a combination thereof. For example, suitable chemical bond enhancements can include silane treatment such as described in U.S. Pat. No. 4,948,366. Suitable mechanical bond enhancements can include ridges, pegs, grooves, particles (such as regularly-shaped particles including spheres, rods, or cones, or irregularly-shaped particles such as shards of ceramic material).

Figure 6B:
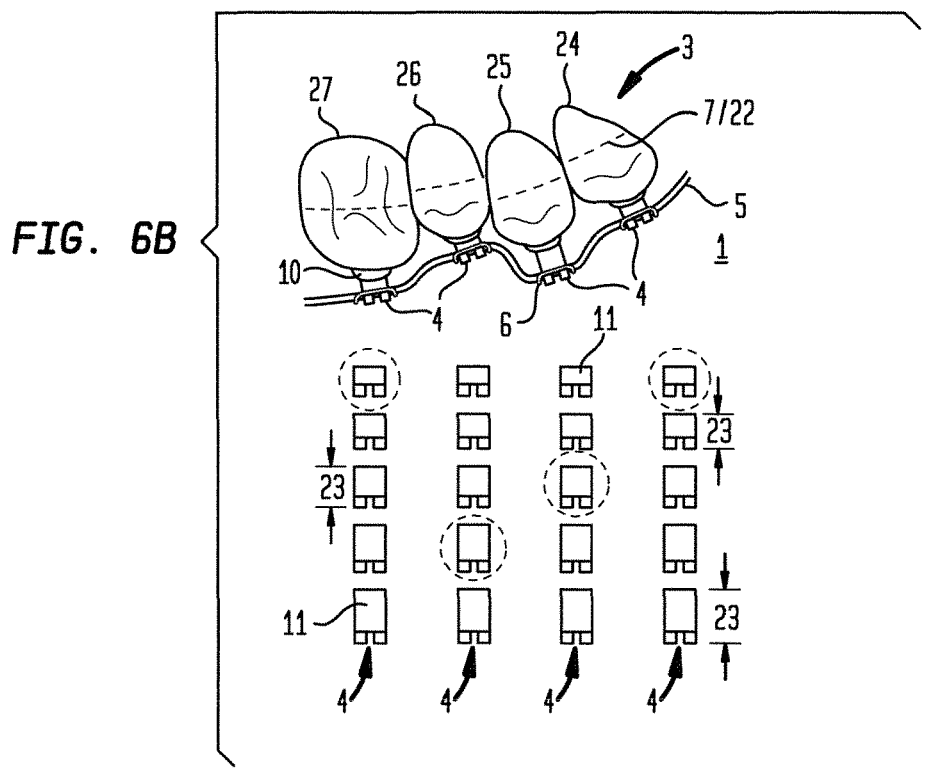
FIG. 6B is an illustration of the inventive bracket system fixed to respective surfaces of the teeth shown in FIG. 6A to correct in-out misalignment of the teeth in relation to the dental arch midline.
Figure 6C:
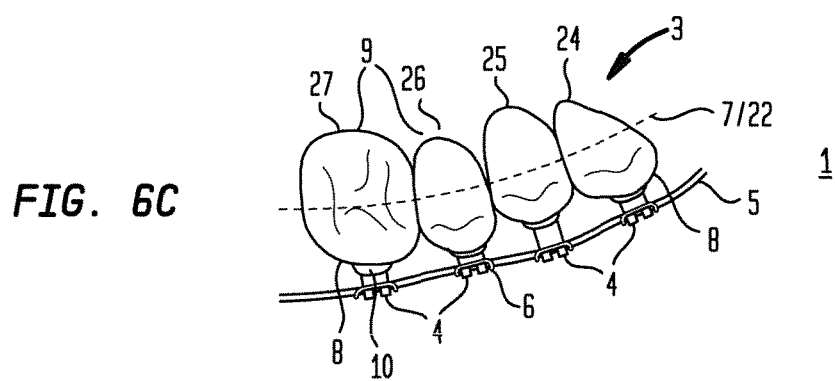
FIG. 6C is an illustration of the correction of in-out misalignment of the teeth in relation to the dental arch midline shown in FIG. 6C following treatment with the inventive bracket system.

Now referring primarily to FIG. 6A through FIG. 6C, the bracket (4) can further include a bracket body (11) having a bracket body length (23) disposed between a bracket body first end (17) and a bracket body second end (18), whereby the bracket body first end (17) couples to the bracket base (10) and the bracket body second end (18) outwardly extends from the bracket base (10). The plurality of brackets (4) within the bracket combinatorial library (33) can have a plurality of preselected bracket body lengths (23) discretely occurring throughout a bracket body length range, typically between zero millimeters to about 5 millimeters. As to particular embodiments, the preselected body bracket lengths (23) discretely occurring throughout the bracket body length range of between zero millimeters to about 5 millimeters can occur at intervals selected from the group including or consisting of: between about 0.25 millimeters to about 0.5 millimeters, between about 0.375 millimeters to about 0.875 millimeters, between about 0.5 millimeters to about 1.0 millimeter, and between about 0.75 millimeters to about 1.25 millimeters, whereby a lesser interval provides a greater number of brackets (4) within the bracket combinatorial library (33) to span the bracket body length range in relation to a greater interval, which provides a lesser number of brackets (4) within the bracket combinatorial library (33) to span the bracket body length range.

Again referring primarily to FIG. 6A through FIG. 6C, when a plurality of brackets (4) are fixedly mounted to a corresponding plurality of teeth (3), the bracket body length (23) can generate in-out force moments, which can urge the teeth (3) to move toward a targeted alignment with a dental arch midline (22). By altering the bracket body length (23), the distance between the facial or lingual surfaces (8)(9) of the respective teeth (3) and an archwire slot base (19) can be correspondingly altered to sufficiently tension an archwire (5) disposed within the archwire slot (12) to move the respective teeth (3) toward the dental arch midline (22), whether "in" or "out".

Now referring to primarily to FIG. 3 and FIG. 6B, the inventive bracket system (1) can provide a graded series of bracket body lengths (23) within a plurality of brackets (4) over a maximum range of action for orthodontic mechanics relating to in-out force moments for alignment of teeth (3) in relation to the dental arch midline (22). Accordingly, an orthodontic practitioner can prescribe and fit a bracket body length (23) (prescription shown in broken circle for each of the plurality of teeth (3)) from the graded series of bracket body lengths (23) within the plurality of brackets (4) of the bracket combinatorial library (33), whereby each bracket body length (23) is unique to the in-out force moments required for alignment of each corresponding one of the plurality of teeth (3) toward the dental arch midline (22). The graded series of bracket body lengths (23) can provide incrementally varying in-out force moments, whereby a greater bracket body length (23) can generate greater in-out force moments in relation to a lesser bracket body length (23), which can generate lesser in-out force moments.

Now referring primarily to FIG. 6A through FIG. 6C, as an illustrative example, a plurality of teeth (3), including a left maxillary cuspid (24), a left maxillary first bicuspid (25), a left maxillary second bicuspid (26), and left maxillary first molar (27), can be misaligned in relation to the dental arch midline (22). As shown in FIG. 6B, to correct this misalignment, the bracket body lengths (23) of the plurality of brackets (4) fixedly mounted to the corresponding plurality of teeth (3) can be prescribed (prescription shown in broken circle for each of the plurality of teeth (3)) such that sufficient in-out force moments can be generated by an archwire (5) disposed within the archwire slot (12) to move the plurality of teeth (3) toward the dental arch midline (22).

As shown in FIG. 6B, to correct the misalignment of the left maxillary first bicuspid (25) and the left maxillary second bicuspid (26) in relation to the dental arch midline (22), a greater bracket base length (23) can be prescribed for the left maxillary first bicuspid (25) to move the left maxillary first bicuspid (25) toward the dental arch midline (22) and a lesser bracket base length (23) can be prescribed for the left maxillary second bicuspid (26) to move the left maxillary second bicuspid (26) toward the dental arch midline (22).

Now referring primarily to FIG. 7A through FIG. 7E, the bracket (4) can further include an archwire slot (12) extending across the bracket body second end (18). The archwire slot (12) can be defined by an archwire slot base (19) joined to a pair of archwire slot walls (20)(21) disposed a distance apart in substantially parallel opposed relation. The archwire slot (12) can be angled in relation to the bracket base (10) to define an archwire slot angle (31), whereby the archwire slot (12) can be configured to receive an archwire (5), such as an archwire (5) having a rectangular archwire cross-section.

Figure 7E:
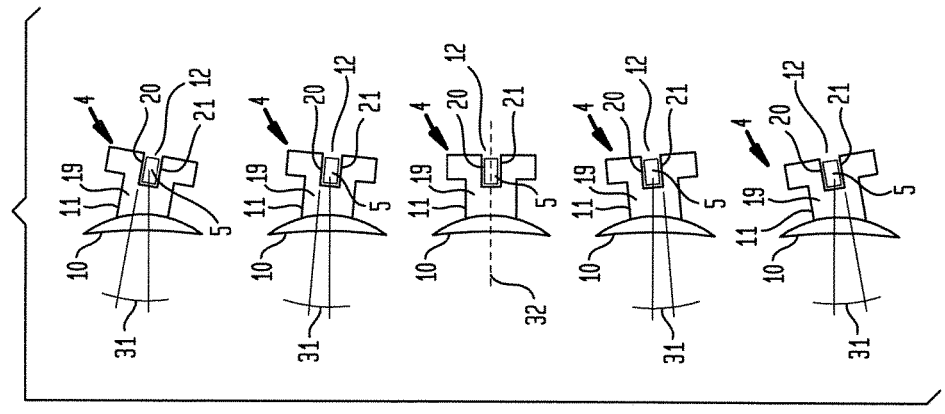
FIG. 7E is an illustration of bracket configuration having a bracket body longitudinal axis angled in relation to a bracket base, the resulting archwire slot angle configured to generate archwire twisting, whether clockwise twisting or counterclockwise twisting, for the correction of torque misalignment of the teeth associated with facial-lingual inclination.
Figure 7D:
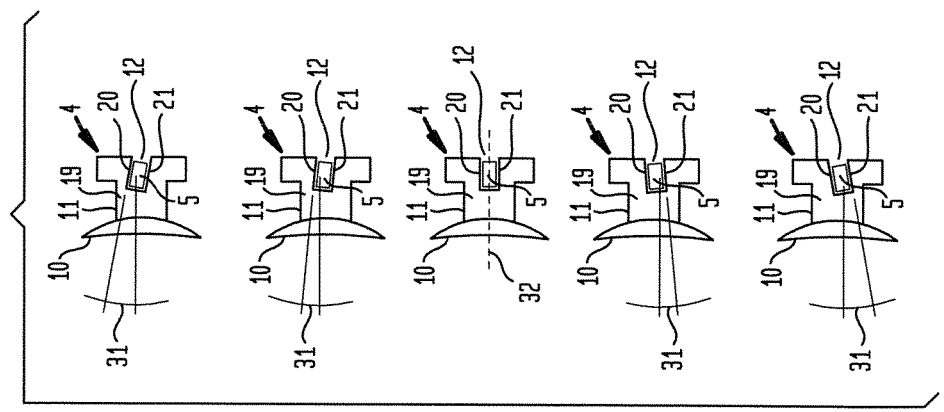
FIG. 7D is an illustration of bracket configuration having an archwire slot angled in relation to a bracket body longitudinal axis, the resulting archwire slot angle configured to generate archwire twisting, whether clockwise twisting or counterclockwise twisting, for the correction of torque misalignment of the teeth associated with facial-lingual inclination.

Now referring primarily to FIG. 7D and FIG. 7E, the archwire slot (12) can be angled in relation to the bracket base (10) to define the archwire slot angle (31) by angling the archwire slot (12) in relation to a bracket body longitudinal axis (32) (as shown in the examples of FIG. 7B and FIG. 7D). Alternatively, the archwire slot (12) can be angled in relation to the bracket base (10) to define the archwire slot angle (31) by angling the bracket body longitudinal axis (32) in relation to the bracket base (10) (as shown in the examples of FIG. 7E).

The plurality of brackets (4) within the bracket combinatorial library (33) can have a plurality of preselected archwire slot angles (31) discretely occurring throughout an archwire slot angle range, typically between 0 degrees to about 60 degrees. As to particular embodiments, the preselected archwire slot angles (31) discretely occurring throughout the archwire slot angle range of between 0 degrees to about 60 degrees can occur at intervals selected from the group including or consisting of: between about 5 degrees to about 10 degrees, between about 7.5 degrees to about 12.5 degrees, between about 10 degrees to about 15 degrees, between about 12.5 degrees to about 17.5 degrees, between about 15 degrees to about 20 degrees, and between about 17.5 degrees to about 22.5 degrees, whereby a lesser interval provides a greater number of brackets (4) within the bracket combinatorial library (33) to span the archwire slot angle range in relation to a greater interval, which provides a lesser number of brackets (4) within the bracket combinatorial library (33) to span the archwire slot angle range.

Now referring primarily to FIG. 7A through FIG. 7C, when a plurality of brackets (4) are fixedly mounted to a corresponding plurality of teeth (3), the archwire slot angle (31) can generate torqueing force moments, which can urge the teeth (3) to move toward a targeted alignment in relation to a zero degree facial-lingual root inclination axis (48). By altering the archwire slot angle (31), the angle between the facial or lingual surfaces (8)(9) of the respective teeth (3) and the archwire slot (12) can be correspondingly altered to sufficiently tension an archwire (5) disposed within the archwire slot (12) to move the respective teeth (3) toward the zero degree facial-lingual root inclination axis (48).

Now referring to primarily to FIG. 3 and FIG. 7B, the inventive bracket system (1) can provide a graded series of archwire slot angles (31) within a plurality of brackets (4) over a maximum range of action for orthodontic mechanics relating to torqueing force moments for alignment of teeth (3) in relation to the zero degree facial-lingual root inclination axis (48). Accordingly, an orthodontic practitioner can prescribe and fit an archwire slot angle (31) (prescription shown in broken circle for each of the plurality of teeth (3)) from the graded series of archwire slot angles (31) within the plurality of brackets (4) of the bracket combinatorial library (33), whereby each archwire slot angle (31) is unique to the torqueing force moments required for alignment of each corresponding one of the plurality of teeth (3) toward the zero degree facial-lingual root inclination axis (48). The graded series of archwire slot angles (31) can provide incrementally varying torqueing force moments, whereby a greater archwire slot angle (31) can generate greater torqueing force moments in relation to a lesser archwire slot angle (31), which can generate lesser torqueing force moments.

Now referring primarily to FIG. 7A through FIG. 7C, as an illustrative example, a plurality of teeth (3), including a left maxillary second bicuspid (26), a left maxillary first bicuspid (25), and a left maxillary first molar (27), can be misaligned in relation to the zero degree facial-lingual root inclination axis (48). As shown in FIG. 7B, to correct this misalignment, the archwire slot angles (31) of the plurality of brackets (4) fixedly mounted to the corresponding plurality of teeth (3) can be prescribed (prescription shown in broken circle for each of the plurality of teeth (3)) such that sufficient torqueing force moments can be generated on an archwire (5) disposed within the archwire slot (12) to move the plurality of teeth (3) toward the zero degree facial-lingual root inclination axis (48).

As shown in FIG. 7B, to correct the misalignment of the left maxillary first bicuspid (25) and the left maxillary second bicuspid (26) in relation to the zero degree facial-lingual root inclination axis (48), a lingual-directing archwire slot angle (31) can be prescribed for the left maxillary first bicuspid (25) to move the left maxillary first bicuspid (25) toward the zero degree facial-lingual root inclination axis (48) and a facial-directing archwire slot angle (31) can be prescribed for the left maxillary second bicuspid (26) to move the left maxillary second bicuspid (26) toward the zero degree facial-lingual root inclination axis (48).

Now referring primarily to FIG. 2A through FIG. 3, the inventive bracket system (1) can include a bracket combinatorial library (33) having a plurality of brackets (4) each interchangeably fixedly mountable to each of a plurality of teeth (3) within a dentition group (34) in a dental arch (7).

Now referring primarily to FIG. 2B, as to particular embodiments, the dental arch (7) can be divided into a first dental arch configuration (49), which includes four dentition groups (34), whereby a first dental arch configuration first dentition group (50) can include central and lateral incisors (51)(52); a first dental arch configuration second dentition group (53) can include cuspids (canine teeth) (54); a first dental arch configuration third dentition group (57) can include first bicuspids (first premolars) (55) and second bicuspids (second premolars) (56); and a first dental arch configuration fourth dentition group (71) can include first and second molars (58)(59).

Now referring primarily to FIG. 2B, as to other particular embodiments, the dental arch (7) can be divided into a second dental arch configuration (60), which includes three dentition groups (34), whereby a second dental arch configuration first dentition group (61) can include central and lateral incisors (51)(52); a second dental arch configuration second dentition group (62) can include cuspids (canine teeth) (54), first bicuspids (first premolars) (55), and second bicuspids (second premolars) (56); and a second dental arch configuration third dentition group (72) can include first and second molars (58)(59).

Now referring primarily to FIG. 2A, as to yet other particular embodiments, the dental arch (7) can be divided into a third dental arch configuration (73), which includes two dentition groups (34), whereby a third dental arch configuration first dentition group (74) can include central and lateral incisors (51)(52), cuspids (canine teeth) (54), first bicuspids (first premolars) (55), and second bicuspids (second premolars) (56); and a third dental arch configuration second dentition group (75) can include first and second molars (58)(59).

As to still yet other particular embodiments, the dental arch (7) can be divided into a fourth dental arch configuration, which only has one dentition group (34), including central and lateral incisors (51)(52), cuspids (canine teeth) (54), first bicuspids (first premolars) (55), second bicuspids (second premolars) (56), and first and second molars (58)(59).

Now referring primarily to FIG. 3, the inventive bracket system (1) can include a bracket combinatorial library (33) including a plurality of brackets (4) each interchangeably fixedly mountable to each of a plurality of teeth (3) within a dentition group (34) in a dental arch (7), whereby each of the plurality of brackets (4) within the bracket combinatorial library (33) can include (i) a bracket base (10) having one configuration fixedly mountable to each one of the plurality of teeth (3) within the dentition group (34); (ii) a bracket body (11) having a preselected bracket body length (23); and (iii) an archwire slot (12) extending across the bracket body second end (18), whereby the archwire slot (12) has a preselected archwire slot angle (31). Each one of the plurality of preselected bracket body lengths (23) can discretely combine with each one of the plurality of preselected archwire slot angles (31) to provide the plurality of brackets (4) within the bracket combinatorial library (33) associated with the dentition group (34), the plurality of brackets (4) being equal to a product of a number of different preselected bracket body lengths (23) occurring throughout the bracket body length range times a number of different preselected archwire slot angles (31) occurring throughout the archwire slot angle range.

Again referring primarily to FIG. 3, the bracket combinatorial library (33) can include a plurality of brackets (4) each interchangeably fixedly mountable to each of a plurality of teeth (3) within a dentition group (34) in a dental arch (7), whereby each of the plurality of brackets (4) within the bracket combinatorial library (33) can include: (i) a bracket base (10) having one configuration fixedly mountable to each one of the plurality of teeth (3) within the dentition group (34); (ii) a bracket body (11) having one of three preselected bracket body lengths (23), including a first bracket body length (63), a second bracket body length (64), and a third bracket body length (65); and an archwire slot (12) extending across the bracket body second end (18), whereby the archwire slot (12) has one of three preselected archwire slot angles (31), including a first archwire slot angle (66), a second archwire slot angle (67), and a third archwire slot angle (68). Accordingly, the bracket combinatorial library (33) can include nine discretely different bracket configurations, the plurality of brackets (4) within the bracket combinational library (33) being equal to a product of the three different preselected bracket body lengths (23) times the three different preselected archwire slot angles (31). Further, each of the nine discretely different bracket configurations can be rotated to achieve any archwire slot rotation configuration (38) in relation to the zero degree archwire slot rotation axis (37), thus allowing customization of the inventive bracket system (1) with a relatively few discretely different bracket configurations.

Accordingly, the inventive bracket system (1) can provide a bracket combinatorial library (33) including a plurality of brackets (4) having rotatable bracket bases (10) associated with the graded series of bracket body lengths (23) and the graded series of archwire slot angles (31) in various combinations and permutations over a maximum range of action for orthodontic mechanics to correspondingly provide a graded series of prescribable tipping force moments, in-out force moments, and torqueing force moments unique for each of the respective teeth (3) of the plurality of teeth (3) within the dentition group (34).

Figure 8:
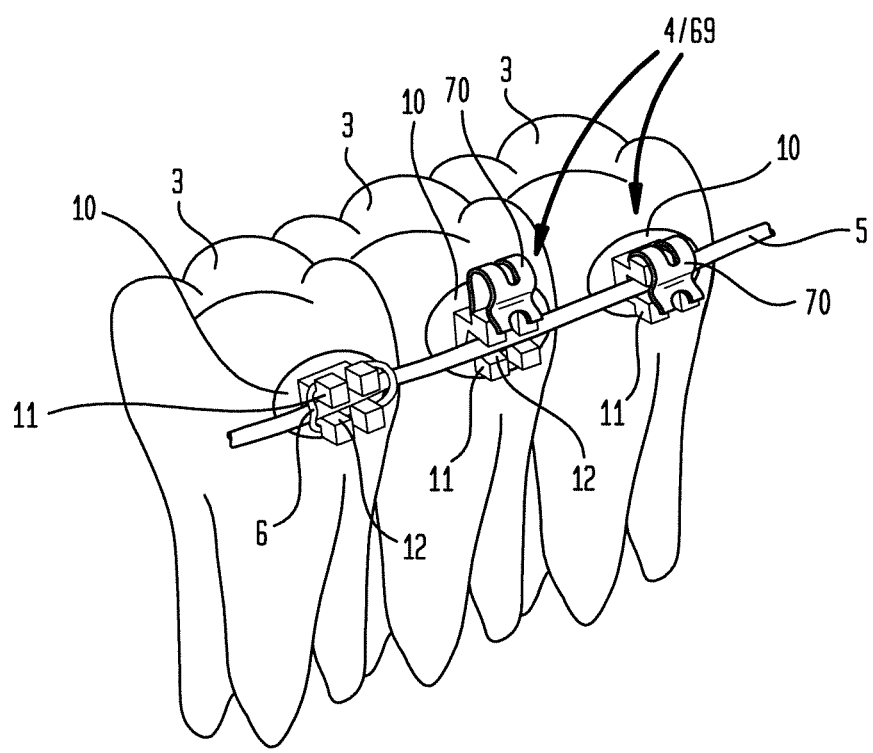
FIG. 8 is an illustration of the inventive bracket system including an elastic ligature and a movable latch element, both adapted to retain the archwire within the archwire slot.

Now referring primarily to FIG. 4A and FIG. 8, as to particular embodiments, the inventive bracket system (1) can further include gingival tie wings (14) and occlusal tie wings (15) which project outwardly from the bracket body second end (18), whereby the gingival tie wings (14) and the occlusal tie wings (15) can be adapted to allow an elastic ligature (6) to be stretched around respective peripheral undercuts (16) to retain the archwire (5) disposed within the archwire slot (12).

Now referring primarily to FIG. 8, as to other particular embodiments, the inventive bracket system (1) can further include self-ligating brackets (69), which can have a movable latch element (70) adapted to retain the archwire (5) within the archwire slot (12). As an illustrative example, the latch element (70) can include a door, a clip, a spring member, a cover, a shutter, a bail, or any other structure which can be connected to the bracket body (11) for retaining the archwire (5) within the archwire slot (12).

A method of producing an inventive bracket system (1) having a bracket combinatorial library (33) can include providing a plurality of brackets (4) each interchangeably fixedly mountable to each of a plurality of teeth (3) within a dentition group (34) in a dental arch (7). Each of the plurality of brackets (4) within the bracket combinatorial library (33) can be provided by configuring a bracket base (10) to have one configuration fixedly mountable to each one of the plurality of teeth (3) within the dentition group (34), the one configuration rotatable throughout a range of between about −50 degrees to about 50 degrees in relation to a zero degree archwire slot rotation axis (37) prior to being fixedly mounted to one of the plurality of teeth (3) within the dentition group (34); providing a bracket body (11) having a bracket body length (23) disposed between a bracket body first end (17) and a bracket body second end (18), whereby the bracket body length (23) can be a preselected bracket body length (23) discretely occurring throughout a bracket body length range of between zero millimeters to about 5 millimeters; coupling the bracket body first end (17) to the bracket base (10), the bracket body second end (18) extending outwardly from the bracket base (10); disposing an archwire slot (12) configured to receive an archwire (5) within the bracket body second end (18) to extend across the bracket body second end (18), the archwire slot (12) defined by an archwire slot base (19) joined to a pair of archwire slot walls (20)(21) disposed a distance apart in substantially parallel opposed relation, the archwire slot (12) angled in relation to the bracket base (10) to define an archwire slot angle (31), whereby the archwire slot angle (31) can be a preselected archwire slot angle (31) discretely occurring throughout an archwire slot angle range of between 0 degrees to about 60 degrees; and discretely combining each one of the plurality of preselected bracket body lengths (23) with each one of the plurality of preselected archwire slot angles (31) to provide the bracket combinatorial library (33), whereby the plurality of brackets (4) within the bracket combinatorial library (33) associated with the dentition group (34) being equal to a product of a number of different preselected bracket body lengths (23) occurring throughout the bracket body length range times a number of different preselected archwire slot angles (31) occurring throughout the archwire slot angle range.

As to particular embodiments of the method of producing an inventive bracket system (1) having a bracket combinatorial library (33), the preselected body bracket lengths (23) discretely occurring throughout the bracket body length range of between zero millimeters to about 5 millimeters can occur at intervals selected from the group including or consisting of: between about 0.25 millimeters to about 0.5 millimeters, between about 0.375 millimeters to about 0.875 millimeters, between about 0.5 millimeters to about 1.0 millimeter, and between about 0.75 millimeters to about 1.25 millimeters.

As to particular embodiments of the method of producing an inventive bracket system (1) having a bracket combinatorial library (33), the preselected archwire slot angles (31) discretely occurring throughout the archwire slot angle range of between 0 degrees to about 50 degrees can occur at intervals selected from the group including or consisting of: between about 5 degrees to about 10 degrees, between about 7.5 degrees to about 12.5 degrees, between about 10 degrees to about 15 degrees, between about 12.5 degrees to about 17.5 degrees, between about 15 degrees to about 20 degrees, and between about 17.5 degrees to about 22.5 degrees.

As to particular embodiments of the method of producing an inventive bracket system (1) having a bracket combinatorial library (33), the dental arch (7) can be divided into a dental arch configuration having four dentition groups (34), whereby a first dental arch configuration first dentition group (50) can include central and lateral incisors (51)(52); a first dental arch configuration second dentition group (53) can include cuspids (canine teeth) (54); a first dental arch configuration third dentition group (57) can include first bicuspids (first premolars) (55) and second bicuspids (second premolars) (56); and a first dental arch configuration fourth dentition group (71) can include first and second molars (58)(59).

As to other particular embodiments of the method of producing an inventive bracket system (1) having a bracket combinatorial library (33), the dental arch (7) can be divided into a dental arch configuration having three dentition groups (34), whereby a second dental arch configuration first dentition group (61) can include central and lateral incisors (51)(52); a second dental arch configuration second dentition group (62) can include cuspids (canine teeth) (54), first bicuspids (first premolars) (55), and second bicuspids (second premolars) (56); and a second dental arch configuration third dentition group (72) can include first and second molars (58)(59).

As to yet other particular embodiments of the method of producing an inventive bracket system (1) having a bracket combinatorial library (33), the dental arch (7) can be divided into a dental arch configuration having two dentition groups (34), whereby a third dental arch configuration first dentition group (74) can include central and lateral incisors (51)(52), cuspids (canine teeth) (54), first bicuspids (first premolars) (55), and second bicuspids (second premolars) (56); and a third dental arch configuration second dentition group (75) can include first and second molars (58)(59).

As to still yet other particular embodiments of the method of producing an inventive bracket system (1) having a bracket combinatorial library (33), the dental arch (7) can be divided into a fourth dental arch configuration, which only has one dentition group (34), including central and lateral incisors (51)(52), cuspids (canine teeth) (54), first bicuspids (first premolars) (55), second bicuspids (second premolars) (56), and first and second molars (58)(59).

As to particular embodiments, the method of producing an inventive bracket system (1) having a bracket combinatorial library (33) can further include providing the archwire (5) disposable in the archwire slot (12), whereby the archwire (5) can be configured to engage the archwire slot (12) in a fixed configuration to generate increasing tipping force moments with an increase in archwire slot rotation in relation to the zero degree archwire slot rotation axis. Subsequently, the tipping force moments can generate movement of at least one of the plurality of teeth (3) toward a zero degree mesial-distal inclination axis (30).

As to particular embodiments, the method of producing an inventive bracket system (1) having a bracket combinatorial library (33) can further include providing the archwire (5) disposable in the archwire slot (12), whereby the archwire (5) can be configured to engage the archwire slot (12) in a fixed configuration to generate increasing in-out force moments with an increase in bracket body length (23). Subsequently, the in-out force moments can generate movement of at least one of the plurality of teeth (3) toward a targeted alignment in relation to a dental arch midline (22).

As to particular embodiments, the method of producing an inventive bracket system (1) having a bracket combinatorial library (33) can further include providing the archwire (5) disposable in the archwire slot (12), whereby the archwire (5) can be configured to engage the archwire slot (12) in a fixed configuration to generate increasing torquing force moments with an increase in archwire slot angle. Subsequently, the torquing force moments can generate movement of at least one of the plurality of teeth (3) toward a zero degree facial-lingual root inclination axis (48).

As to particular embodiments, the method of producing an inventive bracket system (1) having a bracket combinatorial library (33) can further include providing gingival tie wings (14) and occlusal tie wings (15) which project outwardly from the bracket body second end (18), whereby the gingival tie wings (14) and the occlusal tie wings (15) can be adapted to allow an elastic ligature (6) to be stretched around respective peripheral undercuts (16) to retain the archwire (5) disposed within the archwire slot (12).

As to particular embodiments, the method of producing an inventive bracket system (1) having a bracket combinatorial library (33) can further include movably coupling a latch element (70) to the archwire slot (12) proximate the bracket body second end (18), whereby the latch element (70) can be adapted to retain the archwire (5) disposed within the archwire slot (12).

As can be easily understood from the foregoing, the basic concepts of the present invention may be embodied in a variety of ways. The invention involves numerous and varied embodiments of a bracket system and methods for making and using such bracket systems, including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "torque" should be understood to encompass disclosure of the act of "torqueing"—whether explicitly discussed or not—and, conversely, were there effectively disclosure of the act of "torqueing", such a disclosure should be understood to encompass disclosure of a "torque" and even a "means for torqueing." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the bracket systems herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or ail of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A bracket system comprising:
a bracket combinatorial library including a plurality of brackets, each said bracket including:
a bracket base;
a bracket body having a bracket body length disposed between bracket body first and second ends, said bracket body first end coupled to said bracket base, said bracket body second end extending outwardly from said bracket base; and
an archwire slot extending across said bracket body second end, said archwire slot angled in relation to said bracket base to define an archwire slot angle;
wherein said plurality of brackets includes a plurality of preselected bracket body lengths;
wherein said plurality of brackets includes a plurality of preselected archwire slot angles;
wherein each one of said plurality of preselected bracket body lengths discretely combines with each one of said plurality of preselected archwire slot angles; and
wherein said plurality of brackets are equal to a product of a number of different preselected bracket body lengths times a number of different preselected archwire slot angles.

2. The system of claim 1, wherein each said bracket is mountable to each of a plurality of teeth within a dentition group in a dental arch; and
wherein said dental arch is divided into a dental arch configuration having four dentition groups.

3. The system of claim 2, wherein:
(i) a first dentition group comprises central and lateral incisors;
(ii) a second dentition group comprises cuspids;
(ii) a third dentition group comprises first bicuspids, and second bicuspids; and
(iii) a fourth dentition group comprises first and second molars.

4. The system of claim 1, wherein each said bracket is mountable to each of a plurality of teeth within a dentition group in a dental arch; and
wherein said dental arch is divided into a dental arch configuration having three dentition groups.

5. The system of claim 4, wherein:
(i) a first dentition group comprises central and lateral incisors;
(ii) a second dentition group comprises cuspids, first bicuspids, and second bicuspids; and
(iii) a third dentition group comprises first and second molars.

6. The system of claim 1, wherein each said bracket is mountable to each of a plurality of teeth within a dentition group in a dental arch; and
wherein said dental arch is divided into a dental arch configuration having two dentition groups.

7. The system of claim 6, wherein:
(i) a first dentition group comprises central and lateral incisors, cuspids, first bicuspids, and second bicuspids; and
(ii) a second dentition group comprises first and second molars.

8. The system of claim 1, wherein each said bracket is mountable to each of a plurality of teeth within a dentition group in a dental arch; and
wherein said dental arch is divided into a dental arch configuration having one dentition group comprising central and lateral incisors, cuspids, first bicuspids, second bicuspids, and first and second molars.

9. The system of claim 1, further comprising an archwire disposable in said archwire slot, said archwire configured to engage said archwire slot in a fixed configuration to generate increasing tipping force moments with an increase in archwire slot rotation in relation to a zero degree archwire slot rotation axis.

10. The system of claim 9, wherein said tipping force moments generate movement of at least one of a plurality of teeth toward a zero degree mesial-distal inclination axis.

11. The system of claim 1, further comprising said an archwire disposable in said archwire slot, said archwire configured to engage said archwire slot in a fixed configuration to generate increasing in-out force moments with an increase in bracket body length.

12. The system of claim 11, wherein said in-out force moments generate movement of at least one of a plurality of teeth toward a targeted alignment in relation to a dental arch midline.

13. The system of claim 1, further comprising an archwire disposable in said archwire slot, said archwire configured to engage said archwire slot in a fixed configuration to generate increasing torquing force moments with an increase in archwire slot angle.

14. The system of claim 13, wherein said torquing force moments generate movement of at least one of a plurality of teeth toward a zero degree facial-lingual root inclination axis.

15. The system of claim 1, further comprising gingival tie wings and occlusal tie wings which project outwardly from said bracket body second end, said gingival tie wings and said occlusal tie wings adapted to allow an elastic ligature to be stretched around respective peripheral undercuts to overlay an archwire disposed in said archwire slot.

16. The system of claim 1, furthering comprising a latch element movably coupled to said archwire slot proximate said bracket body second end, said latch element adapted to retain an archwire disposed within said archwire slot.

17. The system of claim 1, wherein said bracket base has a configuration rotatable in relation to a zero degree archwire slot rotation axis prior to being fixedly mounted to one of a plurality of teeth within a dentition group.

18. The system of claim 17, wherein said bracket base has a configuration rotatable throughout a range of between about −50 degrees to about 50 degrees in relation to said zero degree archwire slot rotation axis prior to being fixedly mounted to one of said plurality of teeth within said dentition group.

19. The system of claim 1, wherein said preselected bracket body lengths discretely occur throughout a bracket body length range of between zero millimeters to about 5 millimeters.

20. The system of claim 1, wherein said preselected archwire slot angles discretely occur throughout an archwire slot angle range of between zero degrees to about 60 degrees.

* * * * *